(12) United States Patent
Newman

(10) Patent No.: US 7,552,732 B2
(45) Date of Patent: Jun. 30, 2009

(54) ADULT PERCUTANEOUS EMERGENCY TRACHEOTOMY KIT

(76) Inventor: Cyril Newman, 11906 Yorkshire, Richland, MI (US) 49083

( * ) Notice: Subject to any disclaimer, the term of this patent is extended or adjusted under 35 U.S.C. 154(b) by 473 days.

(21) Appl. No.: 11/248,948

(22) Filed: Oct. 11, 2005

(65) Prior Publication Data

US 2007/0246051 A1    Oct. 25, 2007

(51) Int. Cl.
*A61M 11/00*    (2006.01)
(52) U.S. Cl. .............................. 128/207.15; 128/207.29
(58) Field of Classification Search ............ 128/207.14, 128/207.15, 207.29
See application file for complete search history.

(56) References Cited

U.S. PATENT DOCUMENTS

| 3,307,551 | A | * | 3/1967 | Violet, Jr. | 128/207.29 |
| 4,440,161 | A | * | 4/1984 | Wadhwa | 128/202.13 |
| 5,352,206 | A | * | 10/1994 | Cushieri et al. | 604/170.01 |
| 6,109,264 | A | * | 8/2000 | Sauer | 128/207.29 |
| 6,298,851 | B1 | * | 10/2001 | Parota et al. | 128/207.29 |
| 6,971,382 | B1 | * | 12/2005 | Corso | 128/200.26 |
| 2003/0136414 | A1 | * | 7/2003 | Turnbull | 128/207.29 |

* cited by examiner

*Primary Examiner*—Steven O Douglas
(74) *Attorney, Agent, or Firm*—Price, Heneveld, Cooper, DeWitt & Litton, LLP

(57) ABSTRACT

A compact tool that easily fits into the pocket of an emergency responder, such as an emergency room technician, EMT or military medic, for emergency adult percutaneous tracheotomies that contains a stabilizing device, a sharp pointed tip protectively covered when not in use, a bendable tracheostomy tube attachment that has means for sealing the tube around the tracheostomy site and means for attachment to a ventilation means, such as an ambu bag.

18 Claims, 5 Drawing Sheets

ADULT PERCUTANEOUS EMERGENCY TRACHEOTOMY KIT

FIELD OF THE INVENTION

This invention relates to the field of surgical tools, specifically a uniquely compact and efficient tool for physicians, EMTs and military medics for performing adult percutaneous emergency tracheotomies.

BACKGROUND OF THE INVENTION

A tracheotomy is a surgical procedure in which a cut or opening is made in the windpipe (trachea). The surgeon inserts a tube into the opening to bypass an obstruction to allow air to get into the lungs, or to remove secretions. The term tracheostomy is sometimes used interchangeably with tracheotomy. Strictly speaking, however, tracheostomy usually refers to the opening itself, while a tracheotomy is the actual operation.

A tracheotomy is performed if an insufficient amount of air is getting to the lungs, if the person cannot breathe without help, or is having problems with mucus and other secretions getting into the windpipe because of difficulty swallowing. There are many reasons why air cannot get to the lungs. The patient's windpipe may be blocked by a swelling. He or she may have a severe injury to the neck, nose or mouth. The windpipe may be occluded by a large foreign object. There may be paralysis of the throat muscles or the presence of a tumor. The patient may be in a coma, or need a ventilator to pump air into the lungs for a long period of time.

Doctors perform emergency tracheotomies as last-resort procedures. They are done only if the patient's windpipe is obstructed and the situation is life threatening. There are two different procedures that are called tracheotomies. The first is done only in emergency situations and can be performed quite rapidly. The emergency room physician or surgeon makes a cut in a thin part of the voice box (larynx) call the cricothyroid membrane. A tube is inserted and connected to an oxygen bag. This emergency procedure is sometimes called a cricothyroidotomy.

The second type of tracheotomy takes more time and is usually done in an operating room. The surgeon first makes a cut (incision) in the skin of the neck that lies over the trachea. This incision is in the lower part of the neck between the Adam's apple and top of the breastbone. The neck muscles are separated, and the thyroid gland (which overlies the trachea) is usually cut down the middle. The surgeon identifies the rings of cartilage that make up the trachea and cuts into the tough walls. A metal or plastic tube is inserted through the opening.

In both cases, the tube acts like a windpipe and allows the person to breathe. Oxygen or a mechanical ventilator may be hooked up to the tube to bring oxygen to the lungs.

Emergency tracheostomies have been performed for decades, but a tool such as the one described in the instant invention has not been previously available. This invention offers another tool in the armament of the emergency responder, e.g. the emergency room physician, the EMT or the military medic, when emergency tracheostomy must be performed. In addition to being simple to use, it is compact, and easily portable in the pocket of the responder.

SUMMARY OF THE INVENTION

In the preferred embodiment of the invention, an elongated body is described which contains a stabilizing device, a sharp pointed tip protectively covered when not in use, a bendable tracheostomy tube attachment that contains a means for sealing the tube around the tracheostomy site and means for attachment to an external ventilation means, such as an ambu bag.

OBJECT OF THE INVENTION

The principal object of the invention is to provide emergency responders, such as emergency room physicians, EMTs and military medics, a quick, efficient and readily accessible tool for the performance of emergency tracheotomies on adult patients.

DETAILED DESCRIPTION OF AN ENABLING AND PREFERRED EMBODIMENT

Figure 1:
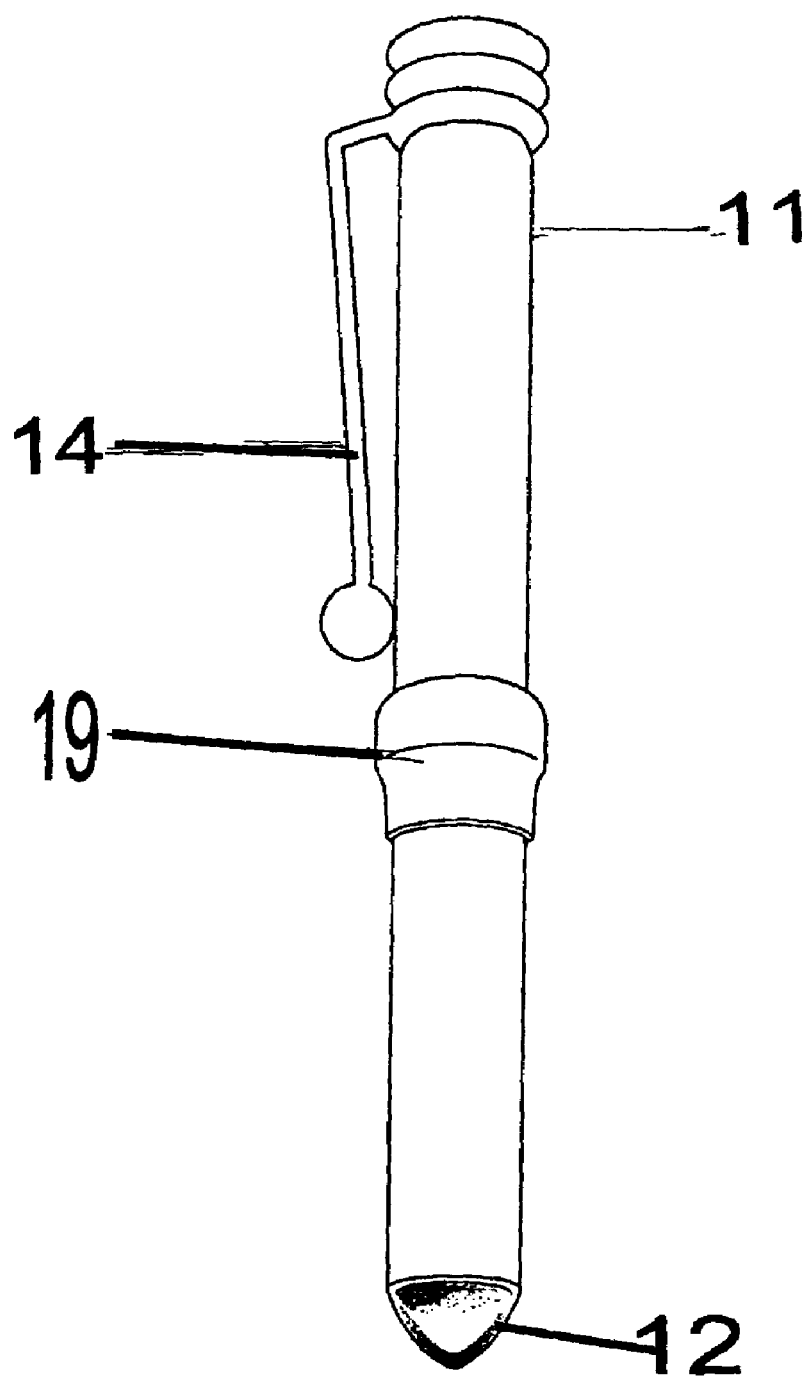
FIG. 1 illustrates a perspective view of the invention without a tracheostomy tube attached to it.
Figure 4:
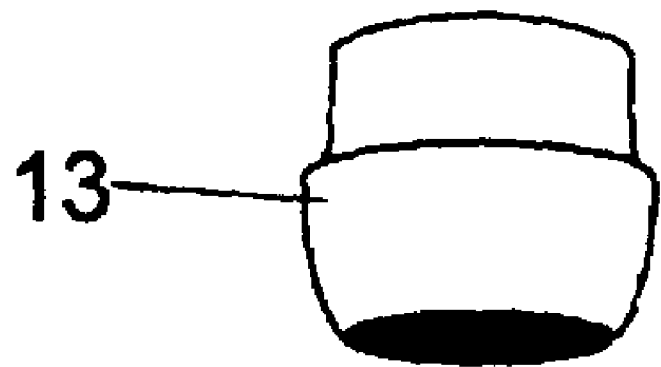
FIG. 4 is the protective cap used to cover the sharp, pointed tip while not in use.

For a better understanding of the invention, turning now to the drawings, FIGS. 1-4 illustrate the device, generally designated as the number 10. FIG. 1 and FIG. 3c are effectively identical. The invention is simple in design and unique in nearly every aspect. The kit is composed of a tubular elongated body 11 with a sharp, pointed tip 12 located at the bottom end of the body 11. The sharp pointed tip 12 is composed of a cone with embedded blade (not shown). The sharp, pointed tip 12 is protected when not use by a cover 13 (FIG. 4). The body 11 is stabilized through the use of a stabilizing means 14 that is oriented up and down the length of the body 11. The stabilizing means 14 resembles a common clip found in fountain pens. It is a rigid member that securably clasps material, such as a pocket or pocket-protector, between the elongated body 11 and the rigid member without deformation or breaking of the rigid member.

Figure 2:
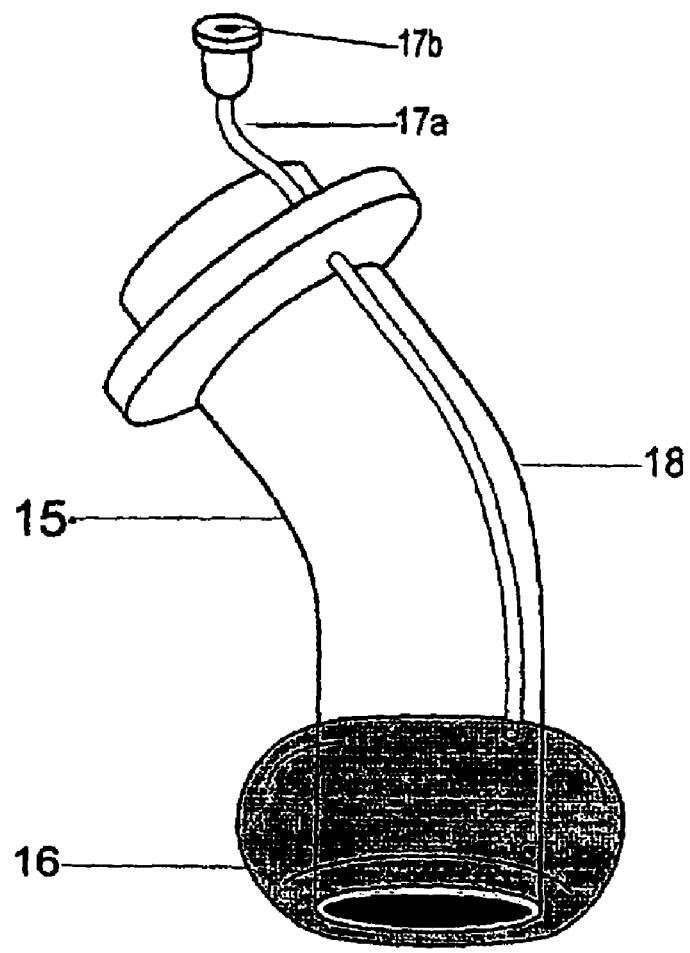
FIG. 2 illustrates the bendable tracheostomy tube that attaches to the invention before the procedure.
Figure 3:
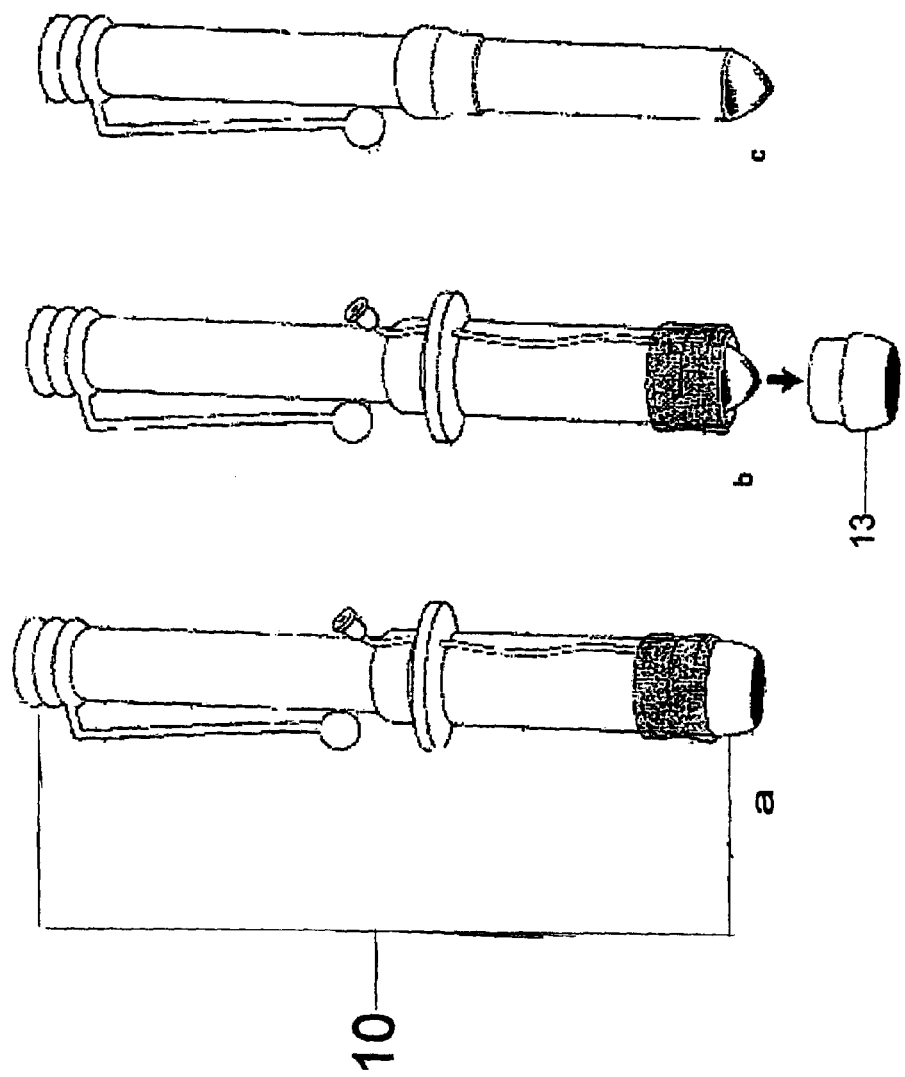
FIG. 3a illustrates the invention with the tracheostomy tube in place and the protective cover over the blade.
FIG. 3b illustrates the invention with the tracheostomy tube in place and the protective cover removed.
FIG. 3c illustrations the invention after the tracheostomy tube has been inserted into the patient and is effectively the same as FIG. 1.
Figure 5:
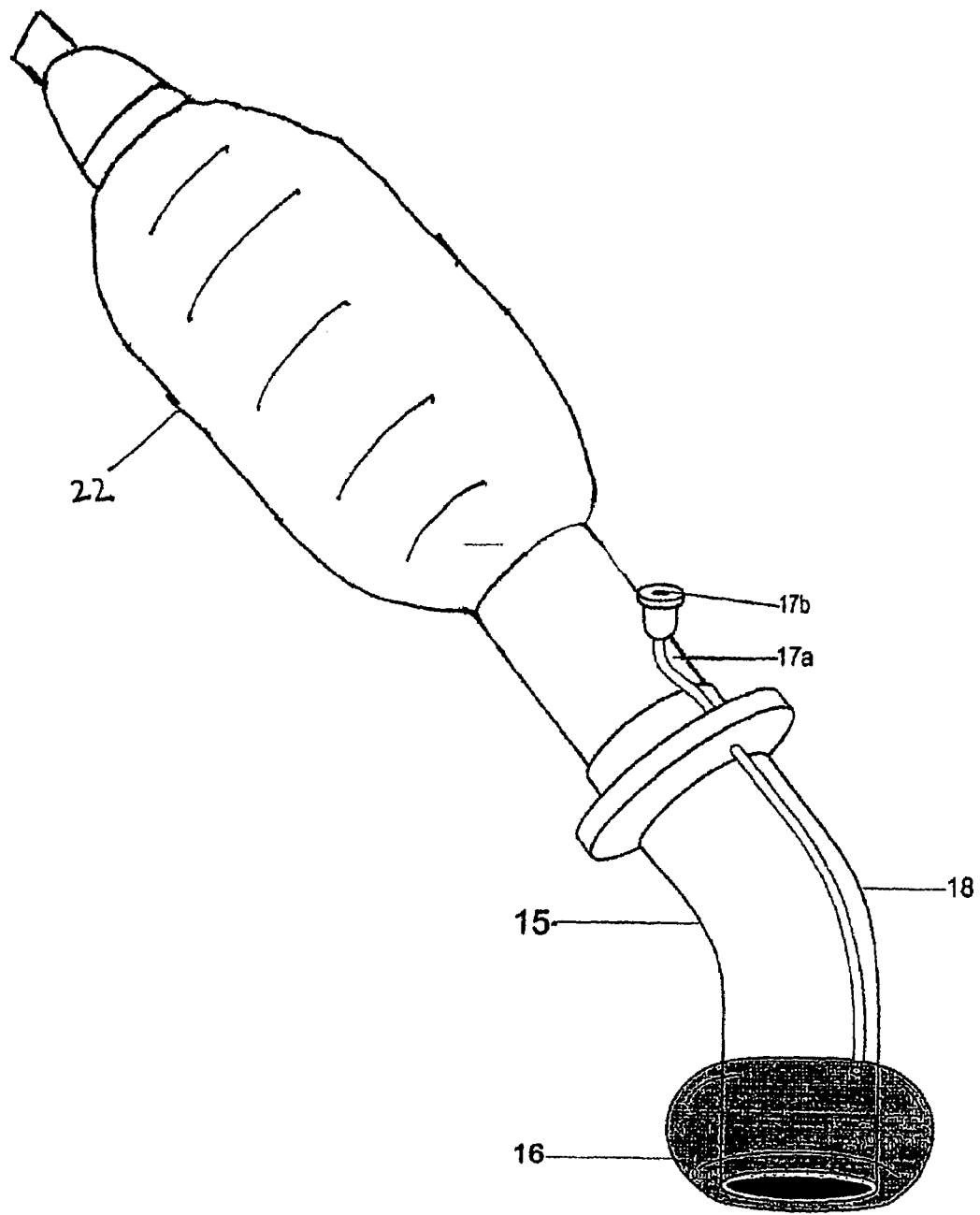
FIG. 5 shows the tracheostomy tube connected to an ambu bag.

FIG. 2 is the tracheostomy tube 15 that attaches to the body 11 in a sleeve-like manner, as illustrated in FIGS. 3a-3b. The tube 15 is made of a bendable material that has its own internal memory, as illustrated in FIG. 2. The tube 15 contains a sealing means 16 to allow for a tight seal around the tracheostomy site on the patient's throat. The tube 15 also contains an inflating means 17 for sealing the sealing means 16, which is usually a balloon collar. The inflating means 17 has an orifice 17b attached to a tube 17a that leads to the balloon collar. The inflating means 17 has an orifice 17b attached to a tube 17a that leads to the balloon collar 16. Pressurized air is sent through the orifice 17b either manually or with a pressurizing device, which then inflates the balloon collar 16, thereby creating a seal around the incision site and allowing for the most efficient flow of air into the patient's lungs. The tracheostomy tube 15 is then attachable to a ventilation means, preferably an ambu bag 22 (see FIG. 5), through the use of a collar 18 designed to attachably fit thereto.

The elongated body 11 also contains a mid-center cuff 19 that wraps around the circumference of the elongated body 11 and is permanently sealed thereto. The cuff 19 prevents the tracheostomy tube 15 from moving up the barrel of the elongated body 11 during the insertion of the tube 15.

The illustrations and examples provided herein are for explanatory purposes and are not intended to limit the scope of the appended claims, as those skilled in the art will make modifications to the invention for particular uses.

I claim:

1. An adult percutaneous emergency tracheotomy kit, comprising
    a tubular elongated body, comprising a sharp, pointed tip and a barrel;
    means for covering said sharp, pointed tip when not in use;
    means for stabilizing said body;
    a tracheostomy tube that is attachable to said body in a sleeve-like manner, comprising:
        an external surface;
        means for sealing the external surface to a surrounding trachea;
        means for inflating said sealing means; and
        means for attaching said tracheostomy tube to a ventilation means; and
    means for preventing said tracheostomy tube from moving up the barrel of said elongated body during insertion of said tube, wherein said preventing means is located midway between proximal and distal ends of said barrel.

2. A kit according to claim 1 wherein said sharp, pointed tip is composed of a cone with an embedded blade.

3. A kit according to claim 1 wherein said means for stabilizing said body comprises a rigid member for securably clasping material between said body and said rigid member without deformation or breaking of said rigid member, having a first end where material is held against said body, and a second end for manually pivoting the rigid member away from said body.

4. A kit according to claim 1 wherein said means for sealing the external surface to a surrounding trachea is an inflatable balloon collar.

5. A kit according to claim 1 wherein said means for inflating said sealing means is an orifice attached to a tube leading to said sealing means that allows for the flow of pressurized air from said inflating means to said sealing means.

6. A kit according to claim 1 wherein said means for attaching said tracheostomy tube to said ventilation means is a collar designed to attachably fit to said ventilation means.

7. A kit according to claim 1 wherein said ventilation means is an ambu bag.

8. A kit according to claim 1 wherein said means for preventing said tracheostomy tube from moving is a cuff located at the mid-center of said body that wraps around the circumference of said body and is permanently sealed to said body.

9. A kit according to claim 1 wherein said tracheostomy tube is composed of material that is bendable after insertion and has internal memory.

10. A method of performing an emergency percutaneous tracheotomy on an adult, comprising
    cutting the trachea of the emergency adult patient with an emergency tracheotomy kit, comprising
        a tubular elongated body, comprising a sharp, pointed tip and a barrel;
        means for covering said sharp, pointed tip when not in use;
        means for stabilizing said body;
        a tracheostomy tube that is attachable to said body in a sleeve-like manner, comprising:
            an external surface;
            means for sealing the external surface to a surrounding trachea;
            means for inflating said sealing means; and
            means for attaching said tracheostomy tube to a ventilation means; and
        means for preventing said tracheostomy tube from moving up the barrel of said elongated body during insertion of said tube, wherein said preventing means is located midway between proximal and distal ends of said barrel;
    inserting said tracheostomy tube into the emergency adult patient; and
    attaching said tracheostomy tube to a ventilation means.

11. A method according to claim 10 wherein said sharp, pointed tip is composed of a cone with an embedded blade.

12. A method according to claim 10 wherein said means for stabilizing said body comprises a rigid member for securably clasping material between said body and said rigid member without deformation or breaking of said rigid member, having a first end where material is held against said body, and a second end for manually pivoting the rigid member away from said body.

13. A method according to claim 10 wherein said means for sealing the external surface to a surrounding trachea is an inflatable balloon collar.

14. A method according to claim 10 wherein said means for inflating said sealing means is an orifice attached to a tube leading to said sealing means that allows for the flow of pressurized air from said inflating means to said sealing means.

15. A method according to claim 10 wherein said means for attaching said tracheostomy tube to said ventilation means is a collar designed to attachably fit to said ventilation means.

16. A method according to claim 10 wherein said ventilation means is an ambu bag.

17. A method according to claim 10 wherein said means for preventing said tracheostomy tube from moving is a cuff located at the mid-center of said body that wraps around the circumference of said body and is permanently sealed to said body.

18. A method according to claim 10 wherein said tracheostomy tube is composed of material that is bendable after insertion and has internal memory.

* * * * *